United States Patent [19]

Lorenz et al.

[11] Patent Number: 5,176,716
[45] Date of Patent: Jan. 5, 1993

[54] HAIR DYE COMPOSITION AND ITS APPLICATION METHOD

[75] Inventors: Heribert Lorenz, Gross-Bieberau; Frank Kufner, Darmstadt; Jürgen Tennigkeit, Seeheim-Jugenheim, all of Fed. Rep. of Germany

[73] Assignee: Goldwell AG, Darmstadt, Fed. Rep. of Germany

[21] Appl. No.: 703,672

[22] Filed: May 21, 1991

[30] Foreign Application Priority Data

Jul. 17, 1990 [DE] Fed. Rep. of Germany ....... 4022724
Dec. 24, 1990 [DE] Fed. Rep. of Germany ....... 4041741

[51] Int. Cl.$^5$ .................................................. A61K 7/13
[52] U.S. Cl. ............................................ 8/405; 8/406; 8/408; 8/409; 8/410; 8/414; 8/416; 8/428; 424/70; 544/226; 544/257; 544/323
[58] Field of Search ............... 8/405, 406, 408, 409, 8/410, 414, 416, 428; 544/226, 257, 323; 424/70

[56] References Cited

U.S. PATENT DOCUMENTS

| Re. 30,199 | 1/1980 | Rose et al. | 8/409 |
|---|---|---|---|
| 2,473,802 | 6/1949 | Kuh et al. | 544/226 |
| 4,043,750 | 8/1977 | Kubersky et al. | 8/409 |
| 4,046,503 | 9/1977 | Kubersky | 8/409 |
| 4,129,413 | 12/1978 | Rose et al. | 8/409 |
| 4,167,633 | 9/1979 | Morrow | 544/323 |
| 4,247,693 | 1/1981 | O'Brien et al. | 544/323 |
| 4,255,574 | 3/1981 | Rosen | 544/323 |
| 4,945,093 | 7/1990 | Maignan et al. | 544/323 |
| 4,985,563 | 1/1991 | Maignan et al. | 544/323 |
| 5,043,446 | 8/1991 | Kikuchi et al. | 544/258 |
| 5,047,405 | 2/1991 | Gennari | 514/249 |

FOREIGN PATENT DOCUMENTS

| 0290819 | 11/1988 | European Pat. Off. |
| 2554456 | 1/1975 | Fed. Rep. of Germany . |
| 2523629 | 12/1976 | Fed. Rep. of Germany . |

*Primary Examiner*—A. Lionel Clingman
*Assistant Examiner*—William S. Parks
*Attorney, Agent, or Firm*—Birch, Stewart, Kolasch & Birch

[57] ABSTRACT

Hair dye composition for oxidative dyeing of human or animal hair containing as developing substances alone or in admixture with other developing substances, a hydroxytriaminopyrimidine, preferably 6-OH-2,4,5-triaminopyrimidine (4-OH-2,5,6-triaminopyrimidine) or 2-OH-4,5,6-triaminopyrimidine and/or a dihydroxydiaminopyrimidine, preferably 2,6-dihydroxy-4,5-diamino-pyrimidine or 4,6-dihydroxy-2,5-diaminopyrimidine.

22 Claims, No Drawings

HAIR DYE COMPOSITION AND ITS APPLICATION METHOD

This invention refers to a composition to dye human or animal hair oxidatively whereby the coloration effect is based on the reaction of certain developing and coupling agents in the presence of hydrogen peroxide or oxygen, as well as to the procedure of application of this composition.

In the field of hair dyeing, oxidation dyestuffs are predominantly employed effecting the coloration by a reaction of certain developing with certain coupling substances in the presence of an appropriate oxidizing agent. In such case different requirements are expected from the oxidation dyestuffs used to dye human hair:

Thus, when oxidative coupling between developing and coupling substances takes place, the desired dyeing shades must be formed in sufficient intensity and permanence, i.e., the coloration must have a good fastness towards light, permanent waving, acids and friction. In addition the coloration shall last adequately and persist for approximately four to six weeks. It should also cause no or at least little harm to the hair structure; moreover, the dyeing components must be harmless as regards toxicity and dermatology.

Dyeing preparations introduced on the market do sometimes not fully achieve the standards mentioned above, e.g., it has been observed that sensitive persons may suffer from sensitization and even allergies, due to the dyeing compounds used. Additionally, when using an alkaline oxidative dyeing preparation, damage to the hair structure has been observed, particularly when the application is repeated as when redyeing several times.

To minimize such damage to the hair structure, acidic hair dyeing compositions have been suggested whereby an originally insufficient dyeing effect in the acidic range could be improved by the addition of low quantities of catalysts, e.g. manganese dioxide (DE-PS 35 30 270); but also these acidic hair dyeing compositions still do not fulfill all requirements.

This invention, therefore, departs from the problem to develop an oxidative hair dyeing composition which meets the standards mentioned to a still higher extent and avoids the disadvantages mentioned above.

The solution of this problem comprises the use of a hydroxytriaminopyrimidine and/or a dihydroxydiaminopyrimidine, preferably 6-hydroxy-2,4,5-triaminopyrimidine (4-hydroxy-4,5,6-triaminopyrimidine), 2-hydroxy-4,5,6-triaminopyrimidine and 5-hydroxy-2,4,6-triaminopyrimidine or 2,6-dihydroxy-4,5-diaminopyrimidine and/or 4,6-dihydroxy-2,5-diaminopyrimidine as developing agent in hair dye compositions.

As a coupling substance for the composition according to the invention, preferably the following agents are used: resorcinol, 4-chlororesorcinol, 3-aminophenol, m-phenylenediamine, 1-naphthol, p-amino-4-hydroxyethylaminoanisole, 2-aminophenol, o-chloro-p-phenylenediamine, 1,7-dihydroxynaphthalene, 3-dimethylaminophenol or mixtures thereof.

As a preferred embodiment of the invention, the quantity of the developing substance should be about 0.05 mol in combination with about the same quantity of the coupling substance in the hair dyeing composition.

The preferred range for the developing substance is from 0.01 to 5, preferably from 0.1 to 4, most preferably from 0.5 to 3% by weight of the dyeing composition (without oxidizer).

The preferred percentage for the coupling substance as defined hereinbefore is within about the same range.

The hair dye composition of the invention may also contain, in addition to triaminohydroxypyrimidines and dihydroxydiaminopyrimidines, conventional coupling agents such as p-phenylene diamine, p-toluylenediamine, tetraaminopyrimidines, 4-aminophenol, etc.

A further advantage of the hair dyeing composition according to the invention is that it is active in the alkaline range as well as in the acidic range, i.e., its formula may be adjusted to a neutral pH value of 7 as well as lower and higher pH-ranges.

When applying the composition according to the invention, it is mixed as usual with an oxidant, preferably hydrogen peroxide, before application.

It has been found that the reaction of the developing with the coupling substance(s) within the dyeing composition may also be effected by means of atmospheric oxygen.

The hair dyeing compositions according to the invention may be prepared in any form appropriate for their application, i.e., creams, emulsions, gels or solutions and also as aerosol foams which may include the usual cosmetic additives such as perfume oils, complexing agents, wetting agents, emulsifyers, thickeners and antioxidants.

The following examples illustrate the hair dyeing composition of the invention in more detail.

A survey on the coupling substances, shading agents, auxiliaries, basic formulas etc. normally used in the preparation of hair dye compositions is found in the monography of K. Schrader, "Grundlagen und Rezepturen der Kosmetika", 2nd edition (1989, Huethig Verlag), pp. 782 to 815, which is incorporated by reference.

EXAMPLE 1

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 4-Hydroxy-2,5,6-triaminopyrimidine | 1.50 g |
| 1-Naphthol | 0.60 g |
| 2-Methylresorcinol | 0.40 g |
| 2-Amino-4-hydroxyethylaminoanisole | 0.40 g |
| 3-Dimethylaminophenol | 0.10 g |
| Ammonia 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed in equal portions with a 6% hydrogen peroxide solution to reach a pH-value of 9.5 and applied onto the hair. After thirty minutes, a bright violet color is achieved.

EXAMPLE 2

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 4-Hydroxy-2,5,6-triaminopyrimidine | 0.85 g |
| 2-Methylresorcinol | 0.10 g |
| 1-Naphthol | 0.10 g |

| | |
|---|---|
| 2-Amino-4-hydroxyethylaminoanisole | 0.25 g |
| 3-Dimethylaminophenol | 0.40 g |
| Sodium hydroxide | 0.30 g |
| Sodium sulphite | 0.25 g |
| Manganese dioxide | 0.60 g |
| Sodium lauryl sulphate | 0.50 g |
| Ethylene diaminotetraacetic acid | 0.20 g |
| Perfume | 0.20 g |
| Demineralized water | ad 100.00 g |

This hair dyeing composition is mixed with a 6% solution of hydrogen peroxide in a proportion of 1:2 to reach a pH-value of 6.8 and applied to the hair. After 30 minutes a bright violet shade is achieved in the dark blonde range.

EXAMPLE 3

| | |
|---|---|
| Oleyl alcohol with 5 moles EO | 1.50 g |
| Stearic acid diethanolamide | 3.00 g |
| 4-Hydroxy-2,5,6-triaminopyrimidine | 0.50 g |
| o-Chloro-p-phenylenediamine | 0.50 g |
| Ethylene diaminotetraacetic acid | 0.10 g |
| Ammonia 25% | 0.50 g |
| Cetyltrimethylammonium chloride | 0.10 g |
| Demineralized water | ad 100.00 g |

This hair dyeing composition has a pH value of 8.5, it is applied onto the hair from an aerosol package using a propane/butane mixture as propellent. After 30 minutes a light blonde golden coloring develops. In this case, the composition is not mixed with an oxidant prior to application; the reaction takes place by oxidation with atmospheric oxygen.

EXAMPLE 4

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 2-Hydroxy-4,5,6-triaminopyrimidine | 1.10 g |
| 2-Aminophenol | 0.55 g |
| 2-Methylresorcinol | 0.55 g |
| Ammonia 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed in equal portions with a 6% solution of hydrogen peroxide (pH-value 9.5) and applied onto the hair. After 30 minutes a bright golden blonde coloring is achieved.

EXAMPLE 5

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 2-Hydroxy-4,5,6-triaminopyrimidine | 1.10 g |
| p-Aminodiphenylamine | 0.55 g |
| 2-Amino-4-hydroxyethylaminoanisole | 0.55 g |
| Ammoniak 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed in equal portions with a 6% solution of hydrogen peroxide (pH 9.5) and applied onto the hair. After 30 minutes a bright brown hair coloring with a blue shade is obtained.

EXAMPLE 6

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 4,5-Diamino-2,6-dihydroxypyrimidine | 0.88 g |
| Resorcinol | 0.10 g |
| 3-Aminophenol | 0.80 g |
| Ammonia 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed with equal portions of a 6% solution of hydrogen peroxide (pH 9.5) and applied onto the hair. After 30 minutes a bright rosewood coloring is achieved.

EXAMPLE 7

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 4,5-Diamino-2,6-dihydroxypyrimidine | 0.88 g |
| 1,5 Naphthalindiol | 0.80 g |
| o-Chloro-p-phenylenediamine | 0.10 g |
| Ammonia 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed in equal portions with a 6% solution of hydrogen peroxide (pH 9.5) and applied onto the hair. After 30 minutes a dark golden brown coloring is obtained.

EXAMPLE 8

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 2,5-Diamino-4,6-dihydroxypyrimidine | 0.88 g |
| 2-Amino-5-methylphenol | 0.40 g |
| 2-Amino-4-hydroxyethylaminoanisole | 0.50 g |
| Ammonia 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed in equal portions with a 6% solution of hydrogen peroxide (pH 9.5) and applied onto the hair. After 30 minutes a bright golden coloring is achieved.

EXAMPLE 9

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 2,5-Diamino-4,6-dihydroxypyrimidine | 0.88 g |
| 2-Amino-5-methylphenol | 0.05 g |
| 2-Amino-4-hydroxyethylaminoanisole | 0.85 g |
| Ammonia 25% | 12.00 g |
| Sodium sulphite | 0.50 g |
| Sodium lauryl sulphate | 0.20 g |
| Ethylene diaminotetraacetic acid | 0.10 g |
| Perfume | 0.20 g |
| Demineralized water | ad 100.00 g |

This hair dyeing composition is mixed in equal portions with a 6% solution of hydrogen peroxide (pH 9.5) and applied onto the hair. After 30 minutes a bright chestnut coloring is achieved.

EXAMPLE 10

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 4,5-Diamino-2,6-dihydroxypyrimidine | 0.78 g |
| 2-Amino-4-hydroxyethylaminoanisole | 0.25 g |
| 2-Methylresorcinol | 0.30 g |
| 1-Hydroxy-3-ethylamino-4-ethylbenzene | 0.25 g |
| Sodium hydroxide | 0.30 g |
| Sodium sulphite | 0.25 g |
| Manganese dioxide | 0.12 g |
| Sodium lauryl sulphate | 0.50 g |
| Ethylene diaminotetraacetic acid | 0.20 g |
| Perfume | 0.20 g |
| Demineralized water | ad 100.00 g |

This hair dyeing composition is mixed with a 6% solution of hydrogen peroxide in a proportion of 1:2. The composition reacts slightly acidic and will produce a bright violet coloring after 30 minutes application.

EXAMPLE 11

| | |
|---|---|
| Cetylstearyl alcohol | 10.00 g |
| Coconut fatty acid monoethanolamide | 2.00 g |
| Stearic acid monoethanolamide | 2.00 g |
| Stearic acid diethanolamide | 1.00 g |
| Oleic acid | 3.00 g |
| 2,5-Diamino-4,6-dihydroxypyrimidine | 0.78 g |
| 1,2,4-Trihydroxybenzole | 0.55 g |
| 2-Amino-4-hydroxyethylaminoanisole | 0.25 g |
| Sodium hydroxide | 0.30 g |
| Sodium sulphite | 0.25 g |
| Manganese dioxide | 0.12 g |
| Sodium lauryl sulphate | 0.50 g |
| Ethylene diaminotetraacetic acid | 0.20 g |
| Perfume | 0.20 g |
| Demineralized water | ad 100.00 g |

This slightly acidic hair dyeing composition is mixed with a 6% solution of hydrogen peroxide in a proportion of 1:2. The application of this composition onto the hair leads to a reddish-brown coloring in the medium blonde range after 30 minutes.

EXAMPLE 12

| | |
|---|---|
| Oleyl alcohol with 5 moles EO | 1.50 g |
| Stearic acid diethanolamide | 3.50 g |
| 4,5-Diamino-2,6-dihydroxypyrimidine | 0.59 g |
| 3-Aminophenol | 0.60 g |
| Ethylene diaminotetraacetic acid | 0.10 g |
| Ammonia 25% | 0.50 g |
| Cetyltrimethylammoniumchloride | 1.00 g |
| Demineralized water | ad 100.00 g |

This hair dyeing composition has a pH value of 8.5 and is applied onto the hair from an aerosol package with a propane/butane mixture as propellent.

After 30 minutes a fashionable red coloring developes. In this case, no oxidant is admixed before the application, but the reaction is effected by oxidation with atmospheric oxygen.

The following tables lists the dyeing results to be expected from combinations of different coupling substances of the invention (hydroxytriaminopyrimidine, dihydroxydiaminopyrimidine). A difference is shown between dyeing preparations to which an oxidizing agent is admixed, and others where oxydation is effected by atmospheric oxygen. A difference is also shown between compositions which are either alkaline or acidic.

The developing substances mentioned in the table have reacted in a concentration of 0.05 mol with the same quantity (0.05 mol) of coupling substances.

Dyeing tests have been made on standardized human hair (60% grey shade), buffalo hair and a wool patch. The compositions were applied for 30 minutes at room temperature in all cases.

After completion of the dyeing process, the test specimens were rinsed at first, then shampooed with a hair shampoo preparation and thereafter dried.

| Example No. | Developing Substance | Coupling Substance | Color of the dyed hair after oxidation with a 6% solution of $H_2O_2$ | | Color of the dyed hair after atmospheric oxidation | |
|---|---|---|---|---|---|---|
| | | | acidic | alkaline | acidic | alkaline |
| 1 | 4,5-Diamino-2,6-dihydroxy-pyrimidine | 4,6-Diamino-o-cresol | red copper | golden yellow | red brown | ochre |
| 2 | 4,5-Diamino-2,6-dihydroxy-pyrimidine | 2,6-Diamino-pyridine | red violet | light red-violet | light aubergine | aubergine |
| 3 | 4,5-Diamino-2,6-dihydroxy-pyrimidine | o-Chlor-p-phenylene-diamine | brown | light brown | yellow | yellow |
| 4 | 4,5-Diamino-2,6-dihydroxy-pyrimidine | 1,5-Naphthalindiol | golden blonde | golden brown | yellow | yellow |

-continued

| Example No. | Developing Substance | Coupling Substance | Color of the dyed hair after oxidation with a 6% solution of H₂O₂ | | Color of the dyed hair after atmospheric oxidation | |
|---|---|---|---|---|---|---|
| | | | acidic | alkaline | acidic | alkaline |
| 5 | 4,5-Diamino-2,6-dihydroxypyrimidine | 2-Aminophenol | orange | brown orange | yellow | yellow |
| 6 | 4,5-Diamino-2,6-dihydroxypyrimidine | N,N-Bis(β-hydroxyethyl-)-m-phenylenediamine | golden brown | golden brown | | |
| 7 | 2,5-Diamino-4,6-dihydroxypyrimidine | 3-Dimethylaminophenol | red violet | red violet | | |
| 8 | 2,5-Diamino-4,6-dihydroxypyrimidine | 2-Aminophenol | orange | golden orange | golden blonde | golden blonde |
| 9 | 2,5-Diamino-4,6-dihydroxypyrimidine | m-Phenylene- | golden brown | golden brown | | |
| 10 | 2,5-Diamino-4,6-dihydroxypyrimidine | 2-Amino-4-hydroxyethylaminoanisole | red brown | brown | | |
| 11 | 2,5-Diamino-4,6-dihydroxypyrimidine | p-Amino-m-cresol | orange | yellow | | |
| 12 | 4-Hydroxy-2,5,6-triaminopyrimidine | Resorcinol | red violet | red | red | light red |
| 13 | 4-Hydroxy-2,5,6-triaminopyrimidine | 4-Chlororesorcinol | red | red | red | light red |
| 14 | 4-Hydroxy-2,5,6-triaminopyrimidine | 3-Aminophenol | red violet | violet | red violet | red |
| 15 | 4-Hydroxy-2,5,6-triaminopyrimidine | m-Phenylenediamine | red violet | red violet | gray violet | light gray violet |
| 16 | 4-Hydroxy-2,5,6-triaminopyrimidine | α-Naphthol | blue violet | blue violet | blue violet | light blue violet |
| 17 | 4-Hydroxy-2,5,6-triaminopyrimidine | p-Amino-o-cresol | red violet | light red violet | red violet | light red violet |
| 18 | 4-Hydroxy-2,5,6-triaminopyrimidine | 2-Amino-4-hydroxyethylaminoanisole | blue | blue | blue | light blue |
| 19 | 4-Hydroxy-2,5,6-triaminopyrimidine | 2-Aminophenol | golden yellow | orange colored | yellow | yellow |
| 20 | 4-Hydroxy-2,5,6-triaminopyrimidine | o-Chloro-p-phenylenediamine | red brown | light brown | light golden yellow | light golden yellow |
| 21 | 4-Hydroxy-2,5,6-triaminopyrimidine | 1,7-Dihydroxynaphthalene | brown | gray brown | gray blue | gray brown |
| 22 | 4-Hydroxy-2,5,6-triaminopyrimidine | 3-Dimethylaminophenol | red violet | violet | red violet | light red violet |
| 23 | 2-Hydroxy-4,5,6-triaminopyrimidine | 2-Amino-4-hydroxyethylaminoanisole | brown violet | golden brown | | |
| 24 | 2-Hydroxy-2,5,6-triaminopyrimidine | m-Phenylenediamine | golden yellow | olive yellow | | |
| 25 | 2-Hydroxy-2,5,6-triaminopyrimidine | 3-Methylresorcin | light violet red | light orange red | | |
| 26 | 2-Hydroxy-2,5,6-triaminopyrimidine | p-Aminodiphenylamine | brown | dark brown | | |
| 27 | 2-Hydroxy-2,5,6-triaminopyrimidine | o-Chloro-p-phenylenediamine | violet brown | red brown | | |

We claim:

1. A hair dye composition for the oxidative dyeing of human hair comprising, as a developing substance, from 0.01 to 5% by weight of the compound 6-hydroxy-2,4,5-triaminopyrimidine (4-hydroxy-2,5,6-triaminopyrimidine) based on the total weight of said hair dye composition and a coupling substance reactive with said developing substance.

2. A hair dye composition for the oxidative dyeing of human hair comprising, as a developing substance, from 0.01 to 5% by weight of the compound 5-hydroxy-2,4,6-triaminopyrimidine based on the total weight of said hair dye composition.

3. A hair dye composition for the oxidative dyeing of human hair comprising, as a developing substance, from 0.01 to 5% by weight of a compound selected from the group consisting of 2,6-dihydroxy-4,5-diaminopyrimidine, 4,6-dihydroxy-2,5-diaminopyrimidine, and mixtures thereof based on the total weight of said hair dye composition and a coupling substance reactive with said developing substance.

4. The composition according to claim 2, further comprising as a coupling substance, resorcinol, 4-chlororesorcinol, 3-aminophenol, 1-naphthol, p-amino-4-hydroxyethylaminoanisole, 2-aminophenol, o-chloro-p-phenylenediamine, 1,7-dyhydroxynaphthalene, 3-dimethyl-aminophenol or mixtures thereof.

5. The composition according to claim 4, wherein said developing substance is contained in a concentration of about 0.05 mol and about the same quantity of coupling substance.

6. A mixture for dyeing human hair comprising mixing a composition according to claim 4 with an oxidant and then applying said mixture onto the hair to be treated.

7. The method for dyeing human hair according to claim 6 wherein said oxidant is hydrogen peroxide.

8. A method for dyeing human hair, comprising applying a composition according to claim 4 onto the hair and effecting oxidation by exposing the ahair to atmospheric oxygen in the surrounding air.

9. The composition according to claim 3, wherein said coupling substance is selected from the group consisting of resorcinol, 4-chlororesorcinol, 3-aminophenol, 1-naphthol, p-amino-4-hydroxyethylaminoanisole, 2-aminophenol, o-chloro-p-phenylenediamine, 1,7-dihydroxynaphthalene, 3-dimethyl-aminophenol and mixtures thereof.

10. The composition according to claim 9, wherein said developing substance is contained in a concentration of about 0.05 mol and about the same quantity of coupling substance.

11. A mixture for dyeing human hair comprising mixing a composition according to claim 9 with an oxidant and then applying said mixture onto the hair to be treated.

12. A method for dyeing human hair comprising applying a composition according to claim 9 onto the hair and effecting oxidation by exposing the hair to atmospheric oxygen in the surrounding air.

13. The composition according to claim 3, wherein the developing substance is 2,6-dihydroxy-4,5-diaminopyrimidine.

14. The composition according to claim 3, wherein the developing substance is 4,6-dihydroxy-2,5-diaminopyrimidine.

15. The composition according to claim 1, wherein said coupling substance is selected from the group consisting of resorcinol, 4-chlororesorcinol, 3-aminophenol, 1-naphthol, p-amino-4-hydroxyethylaminoanisole, 2-aminophenol, o-chloro-p-phenylenediamine, 1,7-dihydroxynaphthalene, 3-dimethyl-aminophenol and mixtures thereof.

16. The composition according to claim 8, wherein the developing substance is contained in a concentration of about 0.05 mol with about the same quantity of coupling substance.

17. A method for dyeing human hair, comprising mixing a composition according to claim 15 with an oxidant; and applying said mixture onto said hair to be treated.

18. The method for dyeing human hair according to claim 17, wherein the oxidant is hydrogen peroxide.

19. A method for dyeing human hair, comprising applying a composition according to claim 15 onto said hair and effecting oxidation by exposing said hair to atmospheric oxygen in the surrounding air.

20. A hair dye composition for the oxidative dyeing of human hair comprising, as a developing substance, the compound 5-hydroxy-2,4,6-triaminopyrimidine, and a coupling substance selected from the group consisting of resorcinol, 4-chlororesorcinol, 3-aminophenol, 1-naphthol, p-amino-4-hydroxyethylaminoanisole, 2-aminophenol, o-chloro-p-phenylenediamine, 1,7-dihydroxynaphthalene, 3-dimethylaminophenol, and mixtures thereof, wherein the concentration of said developing substance is about 0.05 mol. and the concentration of said coupling substance is about the same as the concentration of said developing substance.

21. A hair dye composition for the oxidative dyeing of human hair comprising, as a developing substance, the compound 6-hydroxy-2,4,5-triaminopyrimidine (4-hydroxy-2,5,6-triaminopyrimidine), and a coupling substance selected from the group consisting of resorcinol, 4-chlororesorcinol, 3-aminophenol, 1-naphthol, p-amino-4-hydroxyethylaminoanisole, 2-aminophenol, o-chloro-p-phenylenediamine, 1,7-dihydroxynaphthalene, 3-dimethylaminophenol, and mixtures thereof, wherein the concentration of said developing substance is about 0.05 mol. and the concentration of said coupling substance is about the same as the concentration of said developing substance.

22. A hair dye composition for the oxidative dyeing of human hair comprising a developing substance selected from the group consisting of 2,6-dihydroxy-4,5-diaminopyrimidine, 4,6-dihydroxy-2,5-diaminopyrimidine, and mixtures thereof, and a coupling substance selected from the group consisting of resorcinol, 4-chlororesorcinol, 3-aminophenol, 1-naphthol, p-amino-4-hydroxyethylaminoanisole, 2-aminophenol, o-chloro-p-phenylenediamine, 1,7-dihydroxynaphthalene, 3-dimethylaminophenol and mixtures thereof, wherein the concentration of said developing substance is about 0.05 mol. and the concentration of said coupling substance is about the same as the concentration of said developing substance.

* * * * *